US005599863A

United States Patent [19]

Zimmerman

[11] Patent Number: 5,599,863
[45] Date of Patent: Feb. 4, 1997

[54] GAMMA RADIATION STERILIZABLE ACRYLIC POLYMER

[75] Inventor: Daniel Zimmerman, Stratford, Conn.

[73] Assignee: Cyro Industries, Mt. Arlington, N.J.

[21] Appl. No.: 261,617

[22] Filed: Jun. 17, 1994

[51] Int. Cl.$^6$ ............... C08K 5/10; C08K 5/06; C08K 5/05

[52] U.S. Cl. ............... 524/308; 523/136; 524/310; 524/376; 524/377; 524/378

[58] Field of Search ............... 524/310, 308, 524/377, 378, 317, 910, 911, 376; 523/136; 526/329.7

[56] References Cited

U.S. PATENT DOCUMENTS

| | | | |
|---|---|---|---|
| 2,892,804 | 10/1959 | Crissey | 524/450 |
| 3,048,266 | 8/1962 | Hackhel et al. | 524/308 |
| 3,110,695 | 11/1963 | Ceresa | 260/45.5 |
| 3,261,887 | 7/1966 | Mann et al. | 260/876 |
| 3,271,347 | 9/1966 | Aronoff et al. | 260/31.4 |
| 3,329,557 | 7/1967 | Magat et al. | 161/172 |
| 3,354,238 | 11/1967 | Schmitt et al. | 260/876 |
| 3,392,157 | 7/1968 | Izumi | 524/304 |
| 3,499,950 | 3/1970 | Weitzel et al. | 524/308 |
| 3,655,830 | 4/1972 | Smith | 260/901 |
| 3,940,325 | 2/1976 | Hirao | 524/317 |
| 4,017,452 | 4/1977 | Schwarz . | |
| 4,021,509 | 5/1977 | Murayama et al. | 260/880 R |
| 4,085,166 | 4/1978 | DiLeone et al. | 260/876 |
| 4,228,256 | 10/1980 | Schmitt | 525/302 |
| 4,242,469 | 12/1980 | Schmitt | 525/71 |
| 4,379,190 | 4/1983 | Schenck | 524/308 |
| 4,379,876 | 4/1983 | Clikeman et al. | 524/304 |
| 4,444,934 | 4/1984 | Kasahara et al. | 524/317 |
| 4,588,583 | 5/1986 | Pietsch et al. | 524/317 |
| 4,804,692 | 2/1989 | Lundy et al. | 523/136 |
| 4,873,271 | 10/1989 | Lundy et al. | 523/136 |
| 4,874,802 | 10/1989 | Lundy et al. | 524/378 |
| 5,061,747 | 10/1991 | Roach et al. | 524/379 |
| 5,102,940 | 4/1992 | Keating et al. | 524/379 |
| 5,118,726 | 6/1992 | Mizutani et al. | 523/136 |
| 5,187,208 | 2/1993 | Rodenhouse | 523/136 |
| 5,187,211 | 2/1993 | Lundy et al. | 523/378 |
| 5,214,078 | 5/1993 | Powell et al. | 523/136 |
| 5,216,060 | 6/1993 | Keating et al. | 524/379 |
| 5,248,423 | 9/1993 | Crabb et al. | 523/206 |
| 5,250,589 | 10/1993 | Keating et al. | 523/206 |
| 5,258,423 | 11/1993 | Crabb et al. | 524/317 |
| 5,290,860 | 3/1994 | Zimmerman et al. | 525/67 |
| 5,446,100 | 8/1995 | Durrance et al. | 525/240 |

FOREIGN PATENT DOCUMENTS

| | | |
|---|---|---|
| 0147728A1 | 7/1985 | European Pat. Off. . |
| 0228525A1 | 7/1987 | European Pat. Off. . |
| 2516924A1 | 10/1975 | Germany . |
| 203736 | 11/1983 | Germany . |
| 0149077 | 7/1987 | Germany . |
| 176511 | 9/1981 | Hungary . |
| 39-22597 | 10/1964 | Japan . |
| 51-049246 | 4/1976 | Japan . |
| 56-61448 | 5/1981 | Japan . |
| 04146950 | 6/1992 | Japan . |
| 910799 | 11/1962 | United Kingdom . |

OTHER PUBLICATIONS

Eremeeva et al., "Effect of Low–Molecular–Weight Additives On The Radiation Strength Of Transparent Polymer", *Sov. J. Opt. Technol* 53(6), pp. 361–362, (1986).

Belichenko et al., "On The Mechanism Of Polymer Destruction Under UV–and Gamma–Irradiation: The Influence of Low Molecular Weight Additives Related to Vibrational Cross–Relaxation", *6th Symposium on Radiation Chemistry*, pp. 535–538, (1986).

Krasilova–Vysokomolekuliarnye Soedineniia Seriia B Eng. (1969) 678–81 including translation.

CA85(14):96040 (1976).

*Primary Examiner*—Veronica P. Hoke
*Attorney, Agent, or Firm*—Bart E. Lerman; Claire M. Schultz; Michael J. Kelly

[57] ABSTRACT

Provided are methyl methacrylate polymers admixed with particular polyalkylene glycols, ethers or esters, optionally with BHT, which show good chemical resistance, as well as maintenance of optical properties and minimal yellowing on exposure to sterilizing gamma radiation.

48 Claims, No Drawings

GAMMA RADIATION STERILIZABLE ACRYLIC POLYMER

BACKGROUND OF THE INVENTION

1. Field of the Invention

The present invention relates generally to acrylic polymers which have been modified to resist the degrading effect of sterilizing radiation and, in particular, sterilizing gamma radiation. More specifically, the present invention relates to acrylic polymers admixed with a particular additive or additive combination, which show good chemical resistance, as well as maintenance of optical properties and minimal yellowing on exposure to sterilizing radiation.

2. Description of Related Art

Acrylic polymers based on methyl methacrylate, including impact modified forms, are transparent, processible and possess a number of other physical and chemical properties making them suitable for use as molding resins for the production of a wide variety of useful articles. One such use is in the medical field for forming articles such as syringes, spikes, connectors and luers, suction devices, urine meters, blood plasma separators, drip chambers, cuvettes, dialyzer casings, chest drainage units, bottles for fluids, vaginal speculums, flow valves, aspirators, containers for operating instruments, and the like.

Prior to their use or re-use, these medical articles require sterilization which is commonly accomplished, for example, by exposing the article to low levels of gamma radiation. Doing so, however, induces yellowing and loss of light transmission in the article which alters the appearance in an aesthetically unfavorable way.

One attempt to solve the yellowing problem has been to add to the resin various conventional polymer stabilizing additives such as antioxidants, ultraviolet light absorbers and hindered amines. These conventional stabilizing additives, however, have not in and of themselves been found to effectively control discoloration induced by sterilizing gamma radiation. In addition, the use of such additives may have a detrimental effect on the transparency of articles formed from such resins.

Another proposed solution is described in U.S. Pat. Nos. 102940, 5216060, 5250589 and 5258423, all of which are incorporated by reference herein for all purposes as if fully set forth. In these patents, small amounts (up to 2 wt %) of lower molecular weight alcohols and alcohol derivatives, and particularly aliphatic alcohols and α-hydroxy acids containing up to 10 carbon atoms, as well as ester derivatives thereof, are utilized as additives. Higher molecular weight compounds, and even only slightly higher molecular weight alcohols and ester derivatives such as stearyl alcohol and butyl stearate, are stated not to be effective in promoting resistance to color formation by sterilizing radiation.

While the lower molecular weight additives described in these patents do appear to reduce the gamma radiation induced yellowing of acrylic polymers, their use has not been found to be entirely satisfactory. For example, the use of the lower molecular weight additives (such as butyl lactate) can present handling and processing difficulties in that they are generally liquid, have a tendency to volatilize under common processing conditions, and often have stringent limitations as far as toxicity. In addition, the use of some of these lower molecular weight additives may adversely affect the physical and chemical resistance properties, as well as the optical properties, of the final resin.

An acrylic polymer composition has now been discovered which is not only resistant to gamma radiation induced yellowing but also overcomes many of the defects associated with the aforementioned systems incorporating the lower molecular weight additives.

SUMMARY OF THE INVENTION

In accordance with the present invention, there is provided an acrylic polymer composition comprising, in its overall concept, a methyl methacrylate polymer having incorporated therein, in an amount sufficient to inhibit yellowing of the methyl methacrylate polymer upon exposure to gamma radiation, at one least additive selected from the group consisting of:

(a) at least one polyalkylene glycol additive selected from the group consisting of
 (i) a polyethylene glycol having a number average molecular weight of at least about 200,
 (ii) a polypropylene glycol having a number average molecular weight of at least about 200, and
 (iii) a derivative of (i) or (ii); and
(b) 2,6-ditert.-butyl-p-cresol ("BHT").

Preferably, the methyl methacrylate polymer has incorporated therein at least additive (a). It has been found that, not only does the use of these additives minimize the yellow formation upon gamma irradiation, but also maintains or even improves the transparency properties of the acrylic polymer composition both prior and subsequent to irradiation.

In addition to at least one of the additives (a), it is preferred to utilize a second additive which, upon interaction with gamma radiation, imparts a tint to the methyl methacrylate polymer to indicate that the polymer has been irradiated and to mask any yellow tint which may form as a result thereof. An especially preferred such second additive is BHT which, as indicated above, in and of itself helps minimize yellow formation upon gamma irradiation.

In other aspects, the present invention provides methods for producing such acrylic polymers, as well as articles formed therefrom. Particularly, the present invention provides articles formed from such acrylic polymers which are suitable for use in a variety of medical applications such as set forth above.

These and other features and advantages of the present invention will be more readily understood by those of ordinary skill in the art from a reading of the following detailed description.

DETAILED DESCRIPTION OF THE PREFERRED EMBODIMENTS

Methyl Methacrylate Polymer

The methyl methacrylate polymers suitable for use in accordance with the present invention are substantially thermoplastic polymers containing units derived at least in part from methyl methacrylate, and preferably predominantly from methyl methacrylate, as well as blends thereof with other polymers including impact modifiers. Such methyl methacrylate polymers are well-known to those of ordinary skill in the art, as exemplified by the previously incorporated references, as well as U.S. Pat. Nos. 3,261,887, 3,354,238, 4,085,166, 4,228,256, 4,242,469, 5,061,747 and 5,290,860, all of which are also incorporated by reference herein for all purposes as if fully set forth.

In preferred embodiments, the methyl methacrylate polymers comprise units derived predominantly from methyl methacrylate and, optionally, one or more other free-radically polymerizable monovinyl comonomers including, for example, acrylates and methacrylates other than methyl methacrylate, acrylonitriles and methacrylonitriles, styrenes, vinyl ethers, vinyl halides, olefins and other similar monovinyl compounds. As specific examples suitable comonomers may be mentioned styrene, α-methyl styrene, methyl acrylate, ethyl acrylate, ethyl methacrylate, propyl acrylate, propyl methacrylate, butyl acrylate, butyl methacrylate, acrylonitrile and methacrylonitrile.

In general, the methyl methacrylate polymers preferred for use in the present invention should possess a molecular weight (Mw, weight average) of at least about 50000, and preferably in the range of from about 100000 to about 300000, and a glass transition temperature of at least about 50° C.

As particularly preferred methyl methacrylate polymers may be mentioned copolymers of:

(i) from about 50 to about 90 parts by weight, and more preferably from about 60 to about 80 parts by weight, of methyl methacrylate, (ii) from about 10 to about 40 parts by weight, and more preferably from about 15 to about 30 parts by weight, of styrene, and (iii) 0 to about 25 parts by weight, and more preferably 0 to about 20 parts by weight, of one or more monomers selected from the group consisting of methyl acrylate, ethyl acrylate and acrylonitrile, the total of (i)+(ii)+(iii) comprising 100 parts by weight. As especially preferred specific examples may be mentioned (1) a terpolymer of from about 60 to about 70 parts by weight of methyl methacrylate, about 20 parts by weight of styrene, and about 10 to about 20 parts by weight of acrylonitrile; and (2) a terpolymer of from about 70 to about 80 parts by weight of methyl methacrylate, about 15 to about 25 parts by weight of styrene, and about 5 parts by weight of methyl acrylate or ethyl acrylate.

In another preferred embodiment, the aforementioned methyl methacrylate polymer has incorporated therein an impact modifier to increase the toughness thereof. Such impact modifier should be compatible with the methyl methacrylate polymer so that the two systems can be dispersed into one another in small domain sizes, and should possess a refractive index substantially the same as that of the methyl methacrylate polymer, resulting in a resin with good transparency properties. Suitable such impact modifiers are in general well-known to those of ordinary skill in the art as exemplified in a number of the previously incorporated references.

As a first preferred type of impact modifier may be mentioned a grafted rubber such as a polybutadiene rubber grafted with one or more monomers such as, for example, acrylates and methacrylates, acrylonitriles and methacrylonitriles, styrenes, vinyl ethers, vinyl halides, olefins and other similar monovinyl compounds. As specific examples suitable comonomers may be mentioned styrene, oc-methyl styrene, methyl acrylate, methyl methacrylate, ethyl acrylate, ethyl methacrylate, propyl acrylate, propyl methacrylate, butyl acrylate, butyl methacrylate, acrylonitrile and methacrylonitrile. In general, the weight ratio of rubber to graft monomers in the grafted rubber ranges from about 1:2 to about 6:1, and preferably from about 2:1 to about 4:1.

As a particularly preferred impact modifier of this first type may be mentioned polybutadienes having grafted thereon:

(i) from about 50 to about 95 parts by weight, and more preferably from about 60 to about 85 parts by weight, of methyl methacrylate, (ii) from about 5 to about 40 parts by weight, and more preferably from about 15 to about 30 parts by weight, of styrene, and (iii) 0 to about 25 parts by weight, and more preferably 0 to about 20 parts by weight, of one or more monomers selected from the group consisting of methyl acrylate, ethyl acrylate and acrylonitrile, the total of (i)+(ii)+(iii) comprising 100 parts by weight, and the weight ratio of polybutadiene to graft monomers being in the range of from about 2:1 to about 4:1.

As a second preferred type of impact modifier may be mentioned acrylic copolymers of a core/shell structure, for example, those having a hard core of a poly (alkyl methacrylate), an intermediate stage of a butyl acrylate copolymer, and an outer shell of poly(methyl methacrylate).

The impact modifier may be incorporated into the methyl methacrylate polymer in widely varying amounts depending on the desired end properties, but is typically utilized in amounts of from about 5% to about 25% based upon the combined weight of the methyl methacrylate polymer and impact modifier.

Preferably, the methyl methacrylate polymer (with or without the impact modifier) should possess a transparency of no less than about 70%, and preferably no less than about 80% (as measured in accordance with ASTM D-1003), and a haze of no more than about 15%, and preferably no more than about 10% (as measured in accordance with ASTM D-1003). These transparency and haze requirements also preferably apply to the complete acrylic polymer compositions.

Especially preferred methyl methacrylate polymers for use with the present invention are methyl methacrylate polymers commercially available under the trade designation of ACRYLITE®, and impact modified methyl methacrylate polymers commercially available under the trade designations XT®, CYROLITE® and ACRYLITE PLUS®, of CYRO Industries, Mt. Arlington, N.J.

The aforementioned acrylic polymers may be produced via procedures well-known to those of ordinary skill in the art as exemplified by the previously incorporated references.

Polyalkylene Glycol Additive

As indicated above, the acrylic polymer compositions in accordance with the present invention preferably have incorporated therein at least one polyalkylene glycol additive selected from the group consisting of:

(i) polyethylene glycols having a number average molecular weight of at least about 200, (ii) polypropylene glycols having a number average molecular weight of at least about 200, and (iii) derivatives thereof.

In preferred embodiments, the polyalkylene glycol additives are solid or semisolid at ambient conditions, and more preferably solid, and have number average molecular weights of at least about 600, more preferably at least about 1000, still more preferably in the range of about 1000 to about 20000, and especially in the range of from about 2000 to about 10000.

By "polyethylene glycol" is meant a polyalkylene glycol comprising predominantly ethylene oxide units. In addition to the ethylene oxide units, such polyethylene glycols may also optionally contain lesser amounts of other lower alkylene oxide units such as methylene oxide, propylene oxide and butylene oxide units. By "polypropylene glycol" is meant a polyalkylene glycol comprising predominantly propylene oxide units. In addition to the propylene oxide units, such polyethylene glycols may also optionally contain lesser amounts of other lower alkylene oxide units such as methylene oxide, ethylene oxide and butylene oxide units.

By a "derivative" of a polyalkylene glycol is meant the mono- and di-adducts formed by reacting one or both of the hydroxyl groups of the polyalkylene glycol with, for example, monoalcohols such as methanol, ethanol, propanols, butanols, ethylhexanols and stearyl alcohol (to produce mono- and di-ether adducts); and monoacids such as [adipic acid, phthalic acid,] stearic acid and acetic acid (to produce mono- and di-esters).

Such polyalkylene glycols and derivatives thereof are generally well-known to those of ordinary skill in the art and readily commercially available from numerous sources.

Preferred for use with the present invention are the polyethylene glycols, and particularly the polyethylene glycols comprising essentially ethylene oxide units. Most preferred of these are those having a number average molecular weight of at least about 600, more preferably at least about 1000, and especially at least about 2000. Again, such polyethylene glycols are well-known to those skilled in the art and are readily available articles of commerce.

In general, such polyalkylene glycol additives may be incorporated in widely varying amounts typically ranging from about 0.1 to 10 wt % based upon the weight of the acrylic polymer. Preferably, such additives are incorporated in amounts ranging from about 0.5 to about 8 wt %, and especially in amounts ranging from about 1 to about 7.5 wt %.

Such polyalkylene glycol additives may be incorporated into the acrylic polymer by any commonly utilized method for incorporating additives into such polymers, for example, by blending the components in an extruder. Preferably the method utilized is one that will intimately mix the components so that a substantially uniform mixture thereof occurs.

Other Additives

Instead of or in addition to the polyalkylene glycol additives, the acrylic polymer compositions may have added thereto 2,6-ditert.-butyl-p-cresol (butylated hydroxytoluene, "BHT"), which has been found in and of itself to be effective in minimizing yellow formation upon gamma irradiation. The use of BHT alone, however, may detrimentally affect the transparency of the acrylic polymer, and it is consequently preferred to utilize BHT in combination with one or more of the polyalkylene glycol additives when transparency is an important property for the particular end use. When BHT is utilized, whether alone or in combination with the polyalkylene glycol additives, it is preferably incorporated in amounts from about 0.01 to about 0.5 wt %, more preferably from about 0.05 to about 0.35 wt %, and especially from about 0.1 to about 0.25 wt %, based on the weight of the methyl methacrylate polymer.

In addition to the polyalkylene glycol additives and BHT, the acrylic polymers in accordance with the present invention may optionally contain relatively minor amounts of commonly utilized additives, with the proviso that such other additives are compatible with the acrylic polymers. As examples of such other additives may be mentioned lubricants such as stearyl alcohol, stearic acid, butyl stearate and the like; ultraviolet absorbers, hindered amine light stabilizers and antioxidants; plasticizers; fillers; and the like.

In preferred embodiments, an additional additive is utilized in combination with the polyalkylene glycol additive which additional additive, upon interaction with gamma radiation, imparts a tint to the acrylic polymer to indicate that the polymer has been irradiated and to mask any yellow tint which may have formed as a result of such irradiation. Especially preferred for this use is BHT, which imparts an aesthetically pleasing bluish tint to the acrylic polymer upon irradiation.

Articles Formed From the Acrylic Polymers

The acrylic polymers in accordance with the present invention find particular use as resins for shaped articles, which may be formed by any one of a variety of methods common for forming shaped articles from acrylic polymers. Such methods include, for example, molding, injection blow molding, extrusion molding, calendaring, thermoforming, profile extrusion, sheet extrusion and the like. As indicated earlier, an especially preferred use of the acrylic polymers in accordance with the present invention is as a molding resin for use in forming shaped articles for medical applications including, but not limited to, syringes, spikes, connectors and luers, suction devices, urine meters, blood plasma separators, drip chambers, cuvettes, dialyzer casings, chest drainage units, bottles for fluids, vaginal speculums, flow valves, aspirators, containers for operating instruments, and the like.

The foregoing more general discussion will be further exemplified by the following specific examples which are offered by way of illustration and not limitation of the present invention.

EXAMPLES

In these examples, certain abbreviations are utilized which have the meanings indicated as follows:

| | |
|---|---|
| YI | yellowness index as measured in accordance with ASTM D-1003 |
| % trans. | percent transmission as measured in accordance with ASTM D-1003 |
| % haze | percent haze as measured in accordance with ASTM D-1003 |
| Day 0.0 | prior to irradiation |
| Day X.0 | X days subsequent to gamma irradiation |
| PEG-200 | a polyethylene glycol having a number average molecular weight of 200, available commercially from J. T. Baker, Inc. (Phillipsburg, NJ) |
| PEG-3350 | a polyethylene glycol having a number average molecular weight of 3350, available commercially from J. T. Baker, Inc. (Phillipsburg, NJ) |
| BHT | butylated hydroxytoluene (2,6-ditert.-butyl-p-cresol), commercially available under the trade designation Vulkanox ® KB of Miles Inc. (Pittsburg, PA) |
| CONTROL1 | a rubber modified acrylic polymer commercially available under the trade designation CYROLITE ® G20-300 of CYRO Industries (Mt. Arlington, NJ) |
| CONTROL2 | a rubber modified acrylic polymer commercially available under the trade designation CYROLITE ® G20-100 of CYRO Industries (Mt. Arlington, NJ) |

Comparative Example 1

CONTROL 1 was molded into a 2"×3"×⅛" plaque in an injection molding machine (Battenfeld 50 ton or Netstal 90 ton) under the following conditions:

melt temperature of about 420° F. (range 410°–440° F.)

mold temperature of about 100° F. (range 90°–110° F.)

injection pressure of about 12000 psi (range 9000°–15000 psi)

screw speed of 60–100 rpm clamping pressure of about 2.5 tons/sq. in.

An initial measure of the YI, % trans. and % haze of the resulting plaque was then taken (Day 0.0).

The plaque was then gamma irradiated at a dose of about 2.5 Mrad and stored in an opaque envelope under ambient conditions. Periodically, the plaque was removed from the enveloped and the YI, % trans. and % haze were remeasured. The results are set forth below in Tables I (YI), II (% trans.) and III (% haze).

Example 1

CONTROL 1 was melt mixed with 2 wt % PEG-200 in a 30 mm Leistritz twin screw extruder, then molded into plaques and tested as in Comparative Example 1. The results are presented in Tables I–III below.

Example 2

CONTROL 1 was melt mixed with 2 wt % PEG-3350 in a 30 mm Leistritz twin screw extruder, then molded into plaques and tested as in Comparative Example 1. The results are presented in Tables I–III below.

Example 3

CONTROL 1 was blended with 5 wt % PEG-3350 in a 30 mm Leistritz twin screw extruder, then molded into plaques and tested as in Comparative Example 1. The results are presented in Tables I–III below.

Example 4

CONTROL 1 was blended with 0.2 wt % BHT in a 30 mm Leistritz twin screw extruder, then molded into plaques and tested as in Comparative Example 1. The results are presented in Tables I–III below.

Example 5

CONTROL 1 was blended with 0.3 wt % BHT in a 30 mm Leistritz twin screw extruder, then molded into plaques and tested as in Comparative Example 1. The results are presented in Tables I–III below.

Example 6

CONTROL1 was blended with 0.4 wt % BHT in a 30 mm Leistritz twin screw extruder, then molded into plaques and tested as in Comparative Example 1. The results are presented in Tables I–III below.

TABLE I

| | YELLOWNESS INDEX | | | | | | | | |
|---|---|---|---|---|---|---|---|---|---|
| EX. | 0.0 | 1.0 | 3.0 | 7.0 | 10.0 | 14.0 | 17.0 | 21.0 | 24.0 | 28.0 |
| C1 | 1.8 | 12.7 | 11.7 | 11.0 | 10.1 | 9.4 | 8.5 | 7.5 | 7.5 | 7.4 |
| 1 | 5.2 | 13.6 | 12.4 | 11.3 | 10.0 | 9.1 | 9.2 | 8.1 | 7.3 | 7.4 |
| 2 | 1.1 | 8.6 | 7.3 | 6.2 | 6.6 | 5.7 | 5.5 | 4.7 | 5.1 | 5.2 |
| 3 | 0.2 | 7.8 | 6.7 | 5.7 | 5.1 | 4.1 | 3.4 | 2.9 | 3.0 | 2.7 |
| 4 | 1.5 | 1.2 | 1.4 | 1.4 | 1.8 | 1.8 | 1.5 | 1.6 | 2.0 | 2.3 |
| 5 | 1.5 | −0.8 | −0.5 | −0.2 | 0.2 | 0.2 | 0.5 | 1.1 | 1.5 | 1.8 |
| 6 | 1.4 | −6.1 | −5.6 | −4.4 | −3.7 | −3.1 | −2.8 | −2.1 | −1.3 | −0.8 |

TABLE II

| | % TRANSMISSION | | | | | | | | |
|---|---|---|---|---|---|---|---|---|---|
| EX. | 0.0 | 1.0 | 3.0 | 7.0 | 10.0 | 14.0 | 17.0 | 21.0 | 24.0 | 28.0 |
| C1 | 87.4 | 83.5 | 83.8 | 84.3 | 84.7 | 84.0 | 85.2 | 85.4 | 86.1 | 86.4 |
| 1 | 86.7 | 84.2 | 84.3 | 85.1 | 85.3 | 86.0 | 85.7 | 86.3 | 86.8 | 87.1 |
| 2 | 87.5 | 84.6 | 86.9 | 85.5 | 86.2 | 86.3 | 86.7 | 86.9 | 87.4 | 87.6 |
| 3 | 88.8 | 86.5 | 86.7 | 87.3 | 87.6 | 87.1 | 88.1 | 88.7 | 88.8 | 88.9 |
| 4 | 87.3 | 76.9 | 77.5 | 78.6 | 79.5 | 79.5 | 80.9 | 81.6 | 82.4 | 82.9 |
| 5 | 87.2 | 75.5 | 76.5 | 77.7 | 78.8 | 79.2 | 80.1 | 80.9 | 81.4 | 82.1 |
| 6 | 87.3 | 73.3 | 74.3 | 75.9 | 76.9 | 77.1 | 78.5 | 79.6 | 80.5 | 81.3 |

TABLE III

| | % HAZE | | | | | | | | |
|---|---|---|---|---|---|---|---|---|---|
| EX. | 0.0 | 1.0 | 3.0 | 7.0 | 10.0 | 14.0 | 17.0 | 21.0 | 24.0 | 28.0 |
| C1 | 5.7 | 5.8 | 5.8 | 6.0 | 5.6 | 6.5 | 5.9 | 6.3 | 6.5 | 6.5 |
| 1 | 5.3 | 4.6 | 5.1 | 5.4 | 4.6 | 5.2 | 4.7 | 5.0 | 5.8 | 5.1 |
| 2 | 4.3 | 4.4 | 4.5 | 5.1 | 3.8 | 4.1 | 4.3 | 4.6 | 5.1 | 5.0 |
| 3 | 4.8 | 3.9 | 4.6 | 4.5 | 3.9 | 4.6 | 5.0 | 4.2 | 6.2 | 6.0 |
| 4 | 6.4 | 5.9 | 5.7 | 6.0 | 5.7 | 5.9 | 6.2 | 7.1 | 9.3 | 9.7 |
| 5 | 6.7 | 7.6 | 7.3 | 7.5 | 6.8 | 7.8 | 7.6 | 7.5 | 7.3 | 7.5 |
| 6 | 5.9 | 6.0 | 6.2 | 6.1 | 5.5 | 5.9 | 6.0 | 5.8 | 5.7 | 5.5 |

Explanation of Results for Comparative Example 1 and Examples 1–6

Initially, it should be noted, as described above, that the formulation of Examples 1–6 involved an extra heating step (melt blending) as compared to the CONTROL1 example. Such extra heating step, as is well known to those of ordinary skill in the art, is deleterious to the optical properties of the blended resin.

This initial deleterious effect can best be seen in Example 1, whereby the plaque displays a significantly higher initial YI and slightly lower initial % transmission than CONTROL1. At the same time, the plaque surprisingly initially displays a lower % haze. Despite the significantly higher initial YI in the plaque of Example 1, the YI over time surprisingly drops to levels equal to or even slightly below that in the CONTROL1 plaque. Concurrently, despite the lower initial % transmission in the plaque of Example 1, the value over time again surprisingly reaches levels equal to or even slightly higher than that in the CONTROL 1 plaque.

As can be seen from Examples 4–6, the use of BHT alone provided outstanding results in terms of YI; however, the other optical properties of the plaques did suffer somewhat. For this reason, as indicated above, the use of BHT alone is preferred for those applications in which transparency is not considered as critical.

The best overall results were achieved in Examples 2 and 3 with the use of the PEG-3350 additive.

Comparative Example 2

CONTROL2 was molded into plaques and tested as in Comparative Example 1. The results are presented in Tables IV–VI below.

Example 7

CONTROL2 was melt mixed with 3 wt % PEG-3350 and 0.15 wt % BHT in a 30 mm Leistritz twin screw extruder, then molded into plaques and tested as in Comparative Example 1. The results are presented in Tables IV–VI below.

Example 8

CONTROL2 was melt mixed with 5 wt % PEG-3350 and 0.1 wt % BHT in a 30 mm Leistritz twin screw extruder, then molded into plaques and tested as in Comparative Example 1. The results are presented in Tables IV–VI below.

Example 9

CONTROL2 was melt mixed with 5 wt % PEG-3350 and 0.15 wt % BHT in a 30 mm Leistritz twin screw extruder, then molded into plaques and tested as in Comparative Example 1. The results are presented in Tables IV–VI below.

Example 10

CONTROL2 was melt mixed with 5 wt % PEG-3350 and 0.2 wt % BHT in a 30 mm Leistritz twin screw extruder, then molded into plaques and tested as in Comparative Example 1. The results are presented in Tables IV–VI below.

TABLE IV

| EX. | YELLOWNESS INDEX | | | | | | | | | |
| --- | --- | --- | --- | --- | --- | --- | --- | --- | --- | --- |
|  | 0.0 | 2.0 | 4.0 | 8.0 | 10.0 | 14.0 | 17.0 | 21.0 | 25.0 | 31.0 |
| C2 | −1.4 | 11.2 | 10.1 | 9.2 | 8.9 | 7.6 | 7.0 | 6.4 | 5.8 | 5.0 |
| 7 | 0.2 | 4.7 | 3.5 | 3.0 | 3.1 | 2.3 | 2.4 | 2.3 | 2.1 | 2.0 |
| 8 | 0.9 | 7.1 | 5.6 | 5.0 | 5.1 | 4.3 | 4.1 | 3.7 | 3.7 | 3.4 |
| 9 | 0.7 | 3.3 | 2.7 | 2.2 | 2.4 | 1.9 | 1.8 | 1.7 | 1.7 | 1.6 |
| 10 | −0.1 | 1.0 | 0.7 | 0.6 | 0.4 | 0.4 | 0.5 | 0.5 | 0.6 | — |

TABLE V

| EX. | % TRANSMISSION | | | | | | | | | |
| --- | --- | --- | --- | --- | --- | --- | --- | --- | --- | --- |
|  | 0.0 | 2.0 | 4.0 | 8.0 | 10.0 | 14.0 | 17.0 | 21.0 | 25.0 | 31.0 |
| C2 | 87.6 | 82.6 | 83.6 | 83.9 | 84.3 | 84.6 | 84.8 | 85.1 | 85.3 | 85.9 |
| 7 | 89.0 | 80.5 | 82.1 | 83.0 | 83.8 | 84.4 | 85.1 | 85.7 | 86.1 | 87.1 |
| 8 | 88.8 | 82.1 | 83.8 | 84.7 | 85.3 | 86.0 | 86.5 | 87.0 | 87.3 | 87.9 |
| 9 | 88.8 | 81.7 | 83.6 | 84.6 | 85.3 | 86.2 | 86.7 | 87.1 | 87.5 | 88.3 |
| 10 | 88.5 | 81.6 | 83.5 | 84.3 | 85.0 | 85.3 | 85.6 | 85.6 | 86.7 | — |

TABLE VI

| EX. | % HAZE | | | | | | | | | |
| --- | --- | --- | --- | --- | --- | --- | --- | --- | --- | --- |
|  | 0.0 | 2.0 | 4.0 | 8.0 | 10.0 | 14.0 | 17.0 | 21.0 | 25.0 | 31.0 |
| C2 | 7.3 | 8.0 | 8.1 | 7.7 | 6.9 | 7.8 | 7.7 | 8.2 | 8.5 | 8.5 |
| 7 | 3.3 | 4.1 | 4.3 | 4.3 | 3.6 | 4.1 | 4.2 | 4.3 | 4.5 | 4.8 |
| 8 | 2.9 | 3.5 | 3.5 | 3.6 | 3.2 | 3.5 | 3.5 | 3.5 | 3.6 | 3.6 |
| 9 | 3.1 | 3.5 | 3.3 | 3.6 | 3.0 | 3.3 | 3.3 | 3.3 | 3.5 | 3.7 |
| 10 | 4.9 | 4.9 | 4.9 | 4.9 | 5.2 | 5.2 | 5.3 | 5.3 | 5.6 | — |

Explanation of Results for Comparative Example 2 and Examples 7–10

As can be seen from the results, systems can be formulated based on combinations of PEG's and BHT which provide significant overall improvements in YI, % transmission and % haze.

Although the present invention is described with reference to certain preferred embodiments, it is apparent that variations and modifications thereto may be made by those of ordinary skill in the art without departing from the scope of this invention as defined by the appended claims.

I claim:

1. An acrylic polymer composition comprising a melt blend of a methyl methacrylate polymer comprising units derived predominantly from methyl methacrylate and, in an amount sufficient to inhibit yellowing of the methyl methacrylate polymer upon exposure to gamma radiation, at least one polyalkylene glycol additive selected from the group consisting of (i) a polyethylene glycol having a number average molecular weight of at least about 200, (ii) a polypropylene glycol having a number average molecular weight of at least about 200, and (iii) a derivative of (i) or (ii) selected from the group consisting of mono- and di-ether adducts with monoalcohols, and mono- and di-ester adducts with monoacids.

2. The acrylic polymer composition of claim 1, wherein the methyl methacrylate polymer has melt blended therein from about 0.1 to about 10 wt %, based on the weight of the acrylic polymer, of the polyalkylene glycol additive.

3. The acrylic polymer composition of claim 2, wherein the polyalkylene glycol additive is solid at ambient conditions.

4. The acrylic polymer composition of claim 2, wherein the polyalkylene glycol additive has a number average molecular weight of at least about 600.

5. The acrylic polymer composition of claim 4, wherein the polyalkylene glycol additive has a number average molecular weight of at least about 1000.

6. The acrylic polymer composition of claim 5, wherein the polyalkylene glycol additive has a number average molecular weight in the range of from about 1000 to about 20000.

7. The acrylic polymer composition of claim 6, wherein the polyalkylene glycol additive has a number average molecular weight in the range of from about 2000 to about 10000.

8. The acrylic polymer composition of claim 7, wherein the polyalkylene glycol additive is a polyethylene glycol.

9. The acrylic polymer composition of claim 2, wherein methacrylate polymer has incorporated therein an impact modifier.

10. The acrylic polymer composition of claim 2, further comprising a second additive which, upon interaction with gamma radiation, imparts a tint to the methyl methacrylate polymer to indicate that the polymer has been irradiated and to mask any yellow tint which may form as a result thereof.

11. The acrylic polymer composition of claim 2, wherein the methyl methacrylate polymer has melt blended therein from about 0.01 to about 0.5 wt %, based on the weight of the acrylic polymer, of 2,6-ditert.butyl-p-cresol.

12. The acrylic polymer composition of claim 1, wherein the additive is a polyethylene glycol.

13. The acrylic polymer composition of claim 1, possessing a transparency of no less than about 70% and a haze of no more than about 15%.

14. A method of improving the resistance of an acrylic polymer composition comprising a methyl methacrylate polymer, comprising units derived predominantly from methyl methacrylate, to yellowing induced by exposure to gamma radiation, comprising the step of melt blending into the methyl methacrylate polymer, in an amount sufficient to inhibit yellowing of the methyl methacrylate polymer upon exposure to gamma radiation, at least one polyalkylene glycol additive selected from the group consisting of (i) a polyethylene glycol having a number average molecular weight of at least about 200, (ii) a polypropylene glycol having a number average molecular weight of at least about 200, and (iii) a derivative of (i) or (ii) selected from the group consisting of mono- and di-ether adducts with monoalcohols, and mono- and di- ester adducts with monoacids.

15. The acrylic polymer composition of claim 2, possessing a transparency of no less than about 70% and a haze of no more than about 15%.

16. The acrylic polymer composition of claim 13, possessing a transparency of no less than about 80% and a haze of no more than about 10%.

17. The acrylic polymer composition of claim 15, possessing a transparency of no less than about 80% and a haze of no more than about 10%.

18. The method of claim 14, wherein from about 0.1 to about 10 wt %, based on the weight of the acrylic polymer, of the polyalkylene glycol additive is melt blended into the methyl methacrylate polymer.

19. The method of claim 18, wherein the polyalkylene glycol additive is solid at ambient conditions.

20. The method of claim 18, wherein the polyalkylene glycol additive has a number average molecular weight of at least about 600.

21. The method of claim 20, wherein the polyalkylene glycol additive has a number average molecular weight of at least about 1000.

22. The method of claim 21, wherein the polyalkylene glycol additive has a number average molecular weight in the range of from about 1000 to about 20000.

23. The method of claim 22, wherein the polyalkylene glycol additive has a number average molecular weight in the range of from about 2000 to about 10000.

24. The method of claim 18, wherein the polyalkylene glycol additive is a polyethylene glycol.

25. The method of claim 18, wherein the methyl methacrylate polymer has incorporated therein an impact modifier.

26. The method of claim 18, wherein a second additive is incorporated into the methyl methacrylate polymer which, upon interaction with gamma radiation, imparts a tint to the methyl methacrylate polymer to indicate that the polymer has been irradiated and to mask any yellow tint which may form as a result thereof.

27. The method of claim 18, wherein from about 0.01 to about 0.5 wt %, based on the weight of the acrylic polymer, of 2,6-ditert.butyl-p-cresol is melt blended into the methyl methacrylate polymer.

28. The method of claim 14, wherein the additive is a polyethylene glycol.

29. The method of claim 14, wherein the resulting acrylic polymer possesses a transparency of no less than about 70% and a haze of no more than about 15%.

30. The method of claim 18, wherein the resulting acrylic polymer possesses a transparency of no less than about 70% and a haze of no more than about 15%.

31. The method of claim 29, wherein the resulting acrylic polymer possesses a transparency of no less than about 80% and a haze of no more than about 10%.

32. The method of claim 30, wherein the resulting acrylic polymer possesses a transparency of no less than about 80% and a haze of no more than about 10%.

33. A shaped article formed from an acrylic polymer composition comprising a methyl methacrylate polymer, comprising units derived predominantly from methyl methacrylate, having melt blended therein, in an amount sufficient to inhibit yellowing of the methyl methacrylate polymer upon exposure to gamma radiation, at least one polyalkylene glycol additive selected from the group consisting of (i) a polyethylene glycol having a number average molecular weight of at least about 200, (ii) a polypropylene glycol having a number average molecular weight of at least about 200, and (iii) a derivative of (i) or (ii) selected from the group consisting of mono- and di-ether adducts with monoalcohols, and mono- and di-ester adducts with monoacids.

34. The shaped article of claim 33, wherein from about 0.1 to about 10 wt %, based on the weight of the acrylic polymer, of the polyalkylene glycol additive is melt blended into the methyl methacrylate polymer.

35. The shaped article of claim 34, wherein the polyalkylene glycol additive is solid at ambient conditions.

36. The shaped article of claim 34, wherein the polyalkylene glycol additive has a number average molecular weight of at least about 600.

37. The shaped article of claim 36, wherein the polyalkylene glycol additive has a number average molecular weight of at least about 1000.

38. The shaped article of claim 37, wherein the polyalkylene glycol additive has a number average molecular weight in the range of from about 1000 to about 20000.

39. The shaped article of claim 38, wherein the polyalkylene glycol additive has a number average molecular weight in the range of from about 2000 to about 10000.

40. The shaped article of claim 34, wherein the polyalkylene glycol additive is a polyethylene glycol.

41. The shaped article of claim 34, wherein the methyl methacrylate polymer has incorporated therein an impact modifier.

42. The shaped article of claim 34, wherein a second additive is incorporated into the methyl methacrylate polymer which, upon interaction with gamma radiation, imparts a tint to the methyl methacrylate polymer to indicate that the polymer has been irradiated and to mask any yellow tint which may form as a result thereof.

43. The shaped article of claim 34, wherein from about 0.01 to about 0.5 wt %, based on the weight of the acrylic polymer, of 2,6-ditert.butyl-p-cresol is melt blended into the methyl methacrylate polymer.

44. The shaped article of claim 33, wherein the additive is a polyethylene glycol.

45. The shaped article of claim 33, possessing a transparency of no less than about 70% and a haze of no more than about 15%.

46. The shaped article of claim 34, possessing a transparency of no less than about 70% and a haze of no more than about 15%.

47. The shaped article of claim 45, possessing a transparency of no less than about 80% and a haze of no more than about 10%.

48. The shaped article of claim 46, possessing a transparency of no less than about 80% and a haze of no more than about 10%.

* * * * *